US012427278B1

(12) United States Patent
LaCorte

(10) Patent No.: US 12,427,278 B1
(45) Date of Patent: Sep. 30, 2025

(54) HOSE RETAINING DEVICE FOR RETAINING A SLEEP APNEA TUBING OR OTHER MEDICAL HOSE AGAINST THE BODY OF A USER

(71) Applicant: Anthony LaCorte, Lisle, IL (US)

(72) Inventor: Anthony LaCorte, Lisle, IL (US)

( * ) Notice: Subject to any disclaimer, the term of this patent is extended or adjusted under 35 U.S.C. 154(b) by 847 days.

(21) Appl. No.: 17/541,620

(22) Filed: Dec. 3, 2021

Related U.S. Application Data

(60) Provisional application No. 63/125,725, filed on Dec. 15, 2020.

(51) Int. Cl.
*A61M 16/04* (2006.01)
*A61M 25/02* (2006.01)

(52) U.S. Cl.
CPC ......... *A61M 16/0497* (2013.01); *A61M 25/02* (2013.01); *A61M 2025/0253* (2013.01); *A61M 2025/026* (2013.01); *A61M 2025/0273* (2013.01); *A61M 2210/10* (2013.01)

(58) Field of Classification Search
CPC .......... A61M 16/0497; A61M 2210/10; A61M 25/02; A61M 2025/0253; A61M 2025/026; A61M 16/0465; A61M 2210/0625; A61M 16/06; H02G 3/32; F16L 3/00; F16L 3/137; A61B 5/6283; A61F 13/148; A61H 2011/005; A61H 2205/084

See application file for complete search history.

(56) References Cited

U.S. PATENT DOCUMENTS

| 4,807,640 | A | | 2/1989 | Watson et al. |
| 4,895,162 | A | | 1/1990 | Dolliver |
| 5,163,914 | A | * | 11/1992 | Abel ..................... A61M 25/02 128/200.24 |
| 5,205,832 | A | * | 4/1993 | Tuman .............. A61M 16/0488 604/179 |
| 5,244,464 | A | * | 9/1993 | Madden ................ A61M 25/02 604/179 |
| 5,277,194 | A | | 1/1994 | Hosterman et al. |
| 5,295,490 | A | | 3/1994 | Dodakian |
| 5,352,209 | A | * | 10/1994 | Bird ...................... A61M 25/02 604/179 |
| 5,383,475 | A | | 1/1995 | Austin |

(Continued)

OTHER PUBLICATIONS

BreatheWear BreatheBand CPAP Mask Headgear.
Posey Catheter Tube Holder Strap.

*Primary Examiner* — William R Carpenter
*Assistant Examiner* — Robert F Allen
(74) *Attorney, Agent, or Firm* — John Rizvi; John Rizvi, P.A.—The Patent Professor®

(57) ABSTRACT

A hose retaining device is disclosed herein. The hose retaining device includes a strap assembly coupled to a padding portion having a top surface, a protruding member, and a retaining loop. The strap assembly further includes hook portion, a loop portion, and a fastening slot for turning the strap assembly back upon itself to couple the hook portion to the loop portion. The retaining loop includes an underside configured to receive and retain a corrugated tubing having a plurality of sunken portions and a plurality of protruding portions. The hose retaining device is useful for keeping a corrugated tubing item, commonly used in conjunction with a breathing assistance device, out of the way of the user to increase comfort and stability.

14 Claims, 11 Drawing Sheets

(56) References Cited

U.S. PATENT DOCUMENTS

| | | | |
|---|---|---|---|
| 5,403,285 A | 4/1995 | Roberts | |
| 5,669,884 A * | 9/1997 | Bennes | A61M 1/28 604/179 |
| 5,672,159 A * | 9/1997 | Warrick | A61M 16/0683 604/179 |
| 5,853,396 A * | 12/1998 | Bennes | A61M 1/28 604/179 |
| 6,296,164 B1 | 10/2001 | Russo | |
| 6,610,032 B1 | 8/2003 | Prody | |
| 6,807,680 B2 * | 10/2004 | Sloot | A44C 5/0007 119/857 |
| 7,819,120 B2 | 10/2010 | Taylor et al. | |
| 8,066,657 B2 | 11/2011 | Frazer | |
| 8,584,680 B2 | 11/2013 | Crocetti | |
| 8,608,036 B2 * | 12/2013 | Mori | A45F 3/14 224/267 |
| 8,945,007 B2 | 2/2015 | Ghevondlan et al. | |
| 9,198,615 B2 | 12/2015 | Levendowski et al. | |
| 9,492,105 B1 | 11/2016 | Kayyali et al. | |
| 9,504,410 B2 | 11/2016 | Gal | |
| 9,687,195 B2 | 6/2017 | Sims et al. | |
| 9,775,971 B2 | 10/2017 | Hidalgo | |
| 10,034,995 B2 * | 7/2018 | Kooij | F16L 3/13 |
| 2005/0133038 A1 * | 6/2005 | Rutter | A61M 16/0497 128/207.17 |
| 2006/0096596 A1 * | 5/2006 | Occhialini | A61M 16/0069 128/203.12 |
| 2007/0068533 A1 * | 3/2007 | Bierman | A61M 16/0488 128/207.17 |
| 2008/0108948 A1 | 5/2008 | Beaver | |
| 2009/0078259 A1 * | 3/2009 | Kooij | A61M 16/0875 128/205.25 |
| 2011/0230863 A1 | 9/2011 | Lentini | |
| 2014/0237697 A1 | 8/2014 | Corado | |
| 2016/0029905 A1 | 2/2016 | Kovacs | |
| 2016/0089261 A1 * | 3/2016 | Quinn | A61M 16/06 128/848 |
| 2016/0158473 A1 * | 6/2016 | Schuster | A61M 16/0875 128/207.14 |
| 2016/0213878 A1 * | 7/2016 | Browning, Jr. | A61M 16/0875 |
| 2017/0056630 A1 * | 3/2017 | Fee | A61M 25/02 |
| 2018/0289316 A1 | 10/2018 | Goldstein | |
| 2020/0008709 A1 * | 1/2020 | Martin | A61M 16/0666 |
| 2020/0022645 A1 | 1/2020 | Miko | |

\* cited by examiner

HOSE RETAINING DEVICE FOR RETAINING A SLEEP APNEA TUBING OR OTHER MEDICAL HOSE AGAINST THE BODY OF A USER

CROSS-REFERENCE TO RELATED APPLICATIONS

This application claims the benefit of U.S. Provisional Patent Application No. 63/125,725, filed on Dec. 15, 2020, which is incorporated by reference herein in its entirety.

FIELD OF THE INVENTION

The present invention relates generally to medical device accessories, and more particularly, to a device for stabilizing an air supply hose of a breathing apparatus relative to a user's body.

BACKGROUND OF THE INVENTION

A breathing apparatus or system is a device that is configured to deliver a supply of air to a user who may not be able to breathe on their own or requires breathing assistance. There are many different types of breathing apparatuses available today ranging from those designed for surgical applications to others that help supply a nominal amount of purified air or medical oxygen for improved breathing. Regardless of the application, nearly all breathing apparatuses include an entry port (where the user takes in the air supply to their body), a breathing or air supply hose, and an air supply.

Breathing entry ports vary in size and complexity depending on the application. For users who cannot physically breathe on their own, the entry port may be configured as a complex and delicate nozzle designed to slide down the user's trachea. In other applications, a user may need to have a tracheostomy where a physical incision is made on the front of their neck to open up a direct airway for a steady supply of oxygen. In the instance of those who struggle with sleep issues such as sleep apnea, the user may be required to wear a specialized breathing mask that is secured to their face while sleeping. All of these applications involve a breathing or air supply hose or tube that supplies breathing air to the entry port.

In many cases, the air supply hose used is a semi-transparent and corrugated hose that may extend down to an air tank, breathing machine or other air supply. These hoses are common in the cases of those who have had a tracheostomy or those who have sleep apnea and require the use of a CPAP machine. In either of these specific cases, the corrugated hose may be burdensome to manage or uncomfortable to position around their body while sleeping or moving about.

Breathing apparatuses for both tracheostomy patients and sleep apnea patients have been around for decades. In both of these cases, air or breathable gas is provided to a user's airway. In the case of sleep apnea patients, the air may be delivered at an elevated pressure level in order to help open the person's airway and prevent obstructions. In order to do this effectively, a secure seal needs to remain intact around the user's airway and entry port. In the instance that the air supply hose becomes pulled, bent or otherwise shifted, this may place undue drag or leverage on the entry port and cause the seal to become compromised. In the case of the tracheostomy patient, the air supply hose may also become compromised or even dislodged by force, tension, or environmental contaminants.

Ideally, it would be extremely useful to have a retaining device that is configured to comfortably stabilize an air supply hose relative to the user's body. However, most devices known in the art currently either come with uncomfortable retaining mechanisms or fail to secure the air supply hose in all directions.

Accordingly, there is need for a solution to at least one of the aforementioned problems. For instance, there is an established need for a comfortable and adjustable holder device that may secure an air supply hose from a breathing-related machine, tank, or other breathing apparatus in a manner that won't let the hose shift while moving or sleeping.

SUMMARY OF THE INVENTION

The present invention is directed to a hose retaining device for retaining corrugated tubing. The hose retaining device may allow a user to secure a corrugated tube relating to a breathing device or air supply onto their chest so that the tubing may stay in a desired position and not pull against a mask, trachea port, or other breathing implement.

In a first implementation of the invention, the hose retaining device may include a strap assembly connected to a padding portion. The strap assembly may be suited to extend around the chest of a user. The padding portion may include a retaining loop configured to receive a corrugated tubing item and retain the tubing in a desired position over the padding portion.

In a second aspect, the padding portion may include a protruding member. The protruding member may be structured and arranged to fit between one of the sunken portions in the corrugated tubing. As such, the protruding member may frictionally retain the corrugated tubing in a specified longitudinal configuration.

In another aspect, the strap assembly may include a hook portion and a loop portion configured to releasably size the strap assembly around a user.

In another aspect, the hook portion and the loop portion may be positioned on the same side of the strap assembly.

In another aspect, the strap assembly may include a fastening slot configured to receive the opposing end of the belt therethrough in a manner that allows the opposing end to wrap back upon itself via the hook portion and loop portion.

In another aspect, the padding portion may be configured in a generally oval shape.

In another aspect, the protruding member may be positioned in the middle of the padding portion and underneath the retaining loop.

In another aspect, the retaining loop forms a cavity with the padding portion. The materials used may be configured so that the cavity is able to receive and retain a corrugated tubing item therein without letting the corrugated tubing slide out of position.

In another implementation, a hose retaining device may include a strap assembly, removably positionable and securable around a body area of a user, and a retaining loop carried by the strap assembly. The retaining loop may define a cavity. The cavity may be elongately formed along a longitudinal direction and configured to receive a portion of a corrugated tubing therealong. The retaining loop may at least partially prevent swaying of the corrugated tubing relative to the strap assembly and relative to the longitudinal direction. The hose retaining device may further include a protruding member configured to frictionally engage a valley of the corrugated tubing to block a displacement of the portion of the corrugated tubing in the longitudinal direction along the cavity and relative to the strap assembly.

In another aspect, the strap assembly may be removably positionable and securable around a chest area of a user.

In another aspect, the strap assembly may be adjustably securable around the body area of the user.

In another aspect, the strap assembly may include a right strap portion and a left strap portion at opposite sides of the retaining loop. The right strap portion and left strap portion may be configured to adjustably attach to one another.

In another aspect, one of the left and right strap portions may include a fastening slot and the other of the left and right strap portions may be adjustably insertable through the fastening slot and selectively securable to itself at different positions along said other of the left and right strap portions.

In another aspect, the hose retaining device may further include a platform carried by the strap assembly. The platform may be configured to rest against the body area of the user. The retaining loop may be affixed to the platform.

In another aspect, the strap assembly may include a right strap portion and a left strap portion extending from opposite sides of platform. The right strap portion and left strap portion may be configured to adjustably attach to one another.

In another aspect, opposite edges of the retaining loop may be fixedly secured to the strap assembly.

In another aspect, the strap assembly may include a first portion and a second portion, the first portion comprising a first end of the strap assembly and the second portion comprising a second end of the strap assembly opposite to the first end of the strap assembly. The retaining loop may be provided at the first portion of the strap assembly and may include opposite first and second side portions arranged at opposite sides of the cavity. The first side portion may be fixedly secured to the strap assembly. The first side portion of the retaining loop may be arranged closer to a second portion of the strap assembly. The second portion of the retaining loop may be slidably received through a guide slot of the strap assembly. The cavity may be formed between the first side portion and the guide slot. The retaining loop may further include a free end extending outward of the guide slot. The free end of the retaining loop may be connectable to the second portion of the strap assembly such that tightening of the strap assembly around the body area causes the second portion of the strap assembly to pull on the free end of the retaining loop to slide the retaining loop further outward of the guide slot and reduce the size of the cavity.

In another aspect, the first portion of the strap assembly may provide a first free end of the strap assembly.

In another aspect, the second portion of the strap assembly may provide a second free end of the strap assembly.

In another aspect, the free end of the retaining loop may include a second loop. The second portion of the strap assembly may be disconnectably attachable to the second loop.

In another aspect, the second portion of the strap assembly may include a hook, configured to disconnectably hook onto the second loop of the retaining loop.

In another aspect, the second portion of the strap assembly may be disconnectably looped onto itself to adjust a length of the strap assembly.

In another aspect, the second portion of the strap assembly may be slidably looped through a slot of the hook and disconnectably attached to itself.

In another aspect, the protruding member may protrude into the cavity.

In another aspect, the protruding member may be arranged within the cavity.

In another aspect, the protruding member may be affixed to the strap assembly and arranged facing the cavity and facing the retaining loop.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a hose retaining device for retaining a sleep apnea tubing or other air supply hose, or other medical hose, against the body of a user. For example, the hose retaining device may allow a user to stably secure a corrugated tube relating to a breathing device or air supply onto their chest so that the tubing may stay in a desired position and not pull against a mask, trachea port, or other breathing implement.

Figure 4:
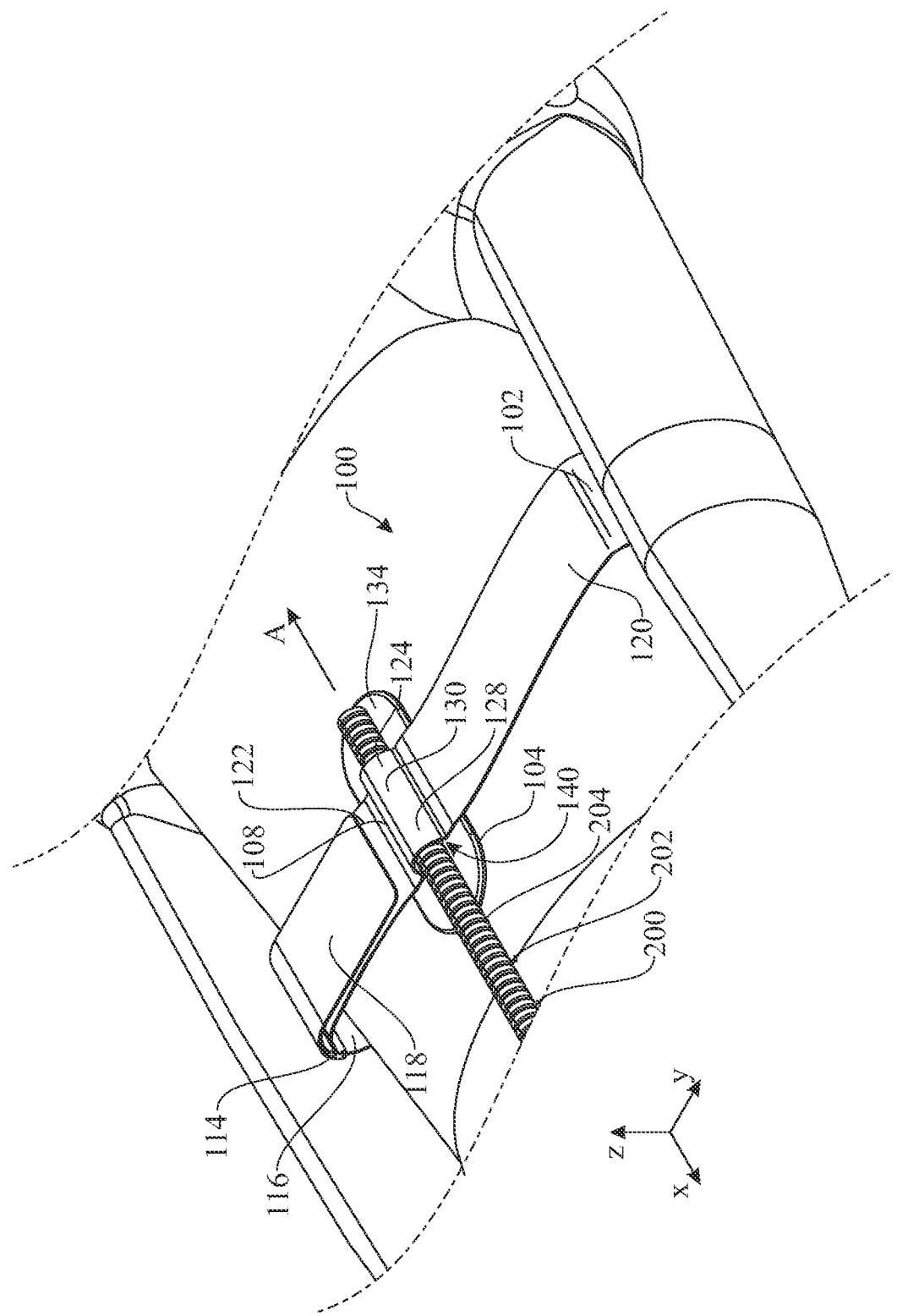
FIG. 4 presents an isometric view of the hose retaining device of FIG. 3, depicting the insertion of a corrugated air supply tube through the elongated cavity defined by the retaining loop of the hose retaining device.
Figure 5:
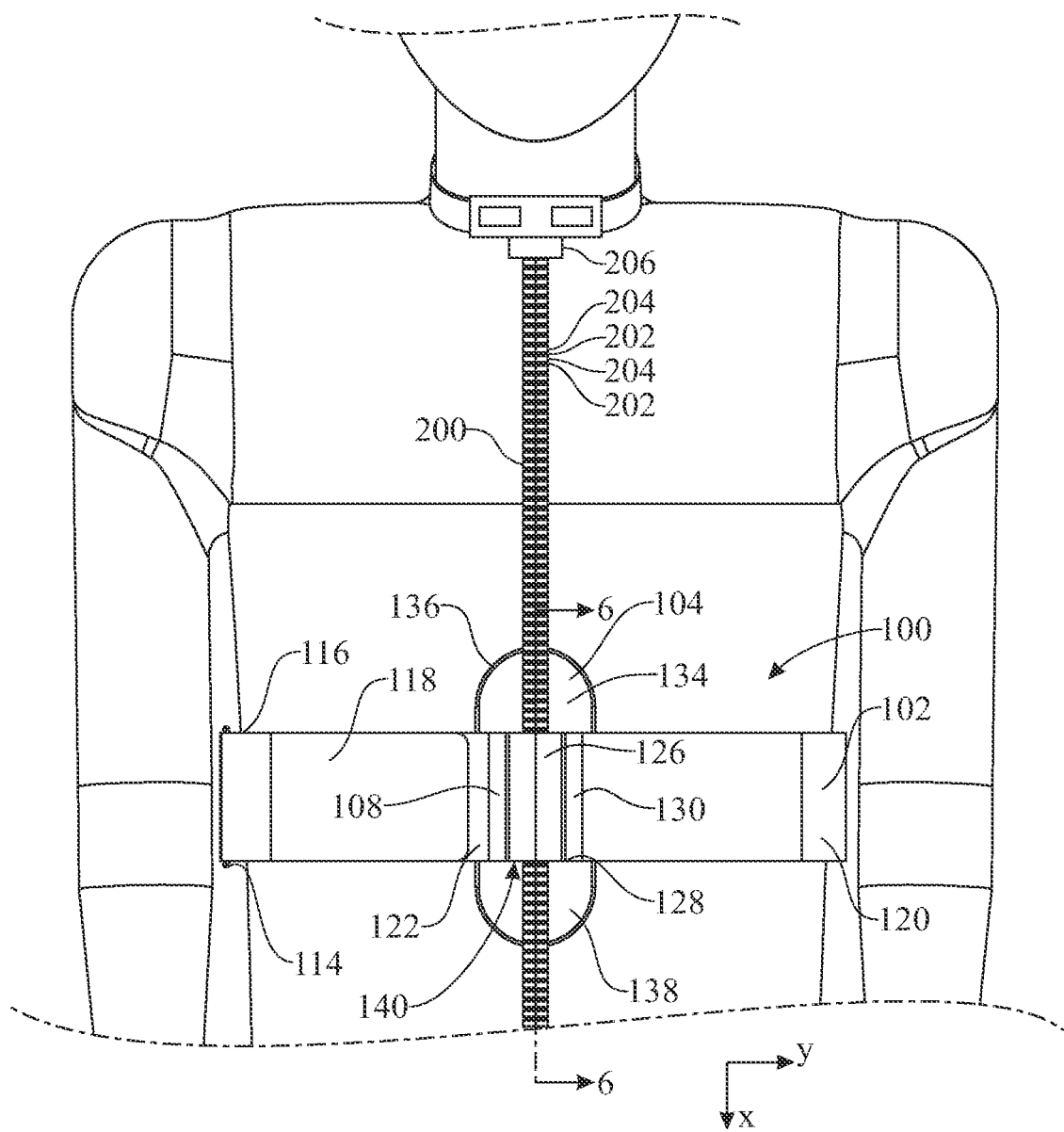
FIG. 5 presents a top plan view of the hose retaining device of FIG. 4, shown fitted around the subject's chest or torso, with the corrugated air supply tube connected to an air entry, and the hose retaining device stabilizing the corrugated air supply tube such that swaying of the corrugated air supply tube is at least partially prevented by the retaining loop.
Figure 6:
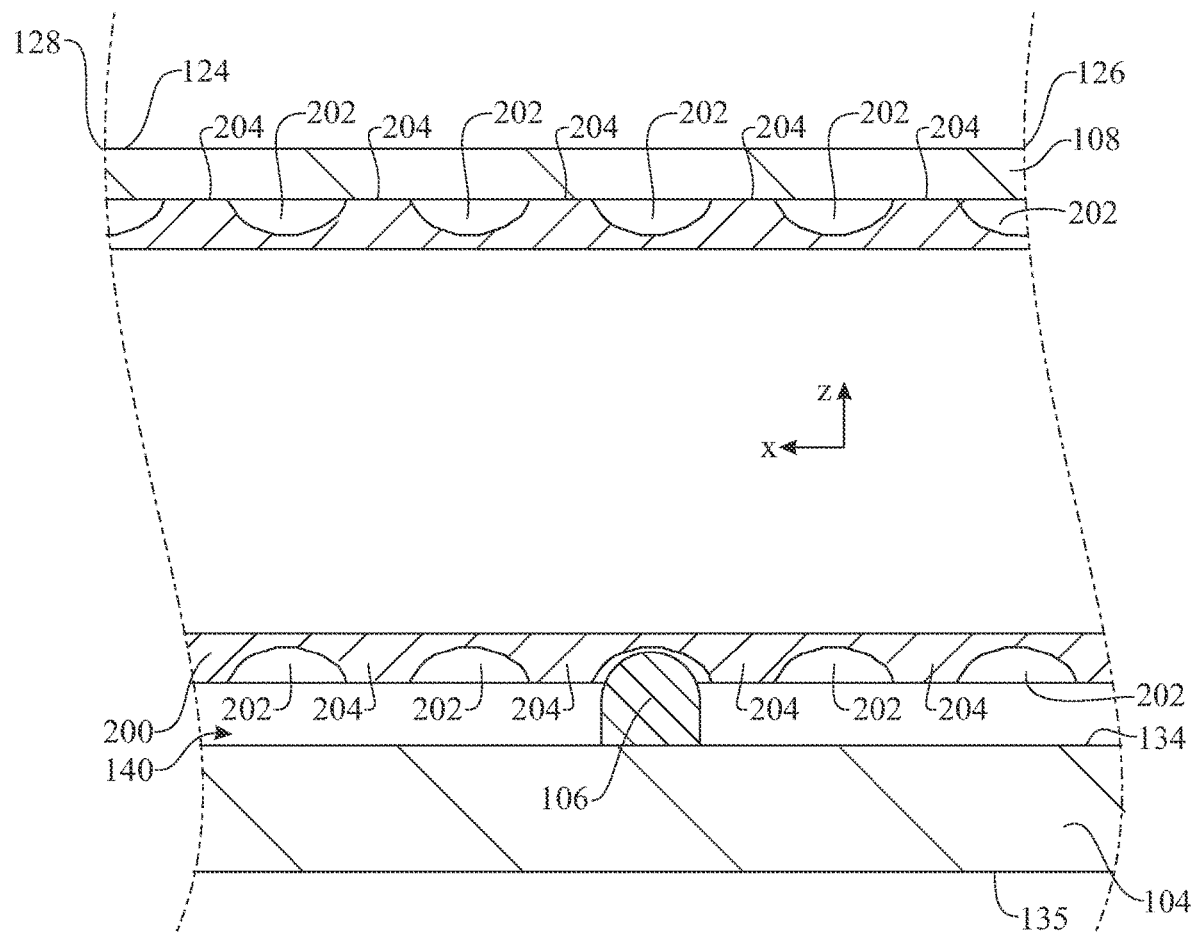
FIG. 6 presents a cross-sectional side elevation view of the retaining loop, padding portion, and protruding member of the hose retaining device of FIG. 1, the cross section taken along section plane 6-6 indicated in FIG. 5, the cross-section showing the protruding member interfacing with the corrugated tubing item to block a longitudinal displacement of the corrugated tubing item.

Referring initially to FIGS. 1-6, a hose retaining device 100 is illustrated in accordance with a first exemplary embodiment of the present invention. As shown, the hose retaining device 100 may include a belt portion or strap assembly 102 which is removably positionable around, and removably securable to, a user's chest or other body area. The strap assembly 102 includes a platform or padding portion 104 which may rest against the user's chest or body area, as shown for instance in FIGS. 2-4. The padding portion 104 depicted herein includes a top surface 134, a bottom surface 135 arranged opposite the top surface 134, an upper top surface 136, an upper bottom surface 137 opposite the upper top surface 136, a lower top surface 138, and a lower bottom surface 139 opposite to the lower top surface 138. A retaining loop 108 is formed over the padding portion 104, defining a channel or cavity 140 therebetween As shown, the strap assembly 102 may be configured to extend in a generally left-to-right or transverse direction y and the cavity 140 may be generally elongated along an upper-to-lower, longitudinal direction x. A protruding member 106 may be arranged inside the cavity 140 and protrude into the cavity 140 relative to adjacent surfaces of the retaining loop 108 or the padding portion 104. For instance, in the present embodiment, the protruding member 106 is affixed to and protrudes upwardly from the top surface 134 of the padding portion 104, as also shown in FIG. 6. In other embodiments, the protruding member 106 may instead be carried by the retaining loop 108, and may protrude downward into the cavity 140. As shown, the protruding member 106 may be elongately formed in the transverse direction y. As best shown in FIG. 6, the protruding member may have an outer convex shape. For example, the outer convex shape may be generally cylindrical. The protruding member 106 may be constructed from metal, plastic, rubber, ceramic, wood, etc.

In some embodiments, such as the present embodiment, the retaining loop 108 is non-removable. In other embodiments, however, the retaining loop 108 may be removable from the hose retaining device 100. For instance and without limitation, the retaining loop 108 may be formed as a separate part, independently of the strap assembly 102, and may be disconnectably secured to strap assembly 102 (for example, to the padding portion 104 of the strap assembly 102), by a hook-and-loop attachment or other disconnectable attachment. In some cases, the retaining loop 108 may be disconnected from the remainder of the hose retaining device 100, and said remainder of the hose retaining device 100 may be disposed, while the retaining loop 108 may be reattached to and reused with a new hose retaining device 100. In this disposable version of the hose retaining device 100 where the retaining loop 108 is reusable, the protruding member 106 may be advantageously affixed to the retaining loop 108 as described heretofore, such that the protruding member 106 is reusable together with the retaining loop 108.

Figure 1:
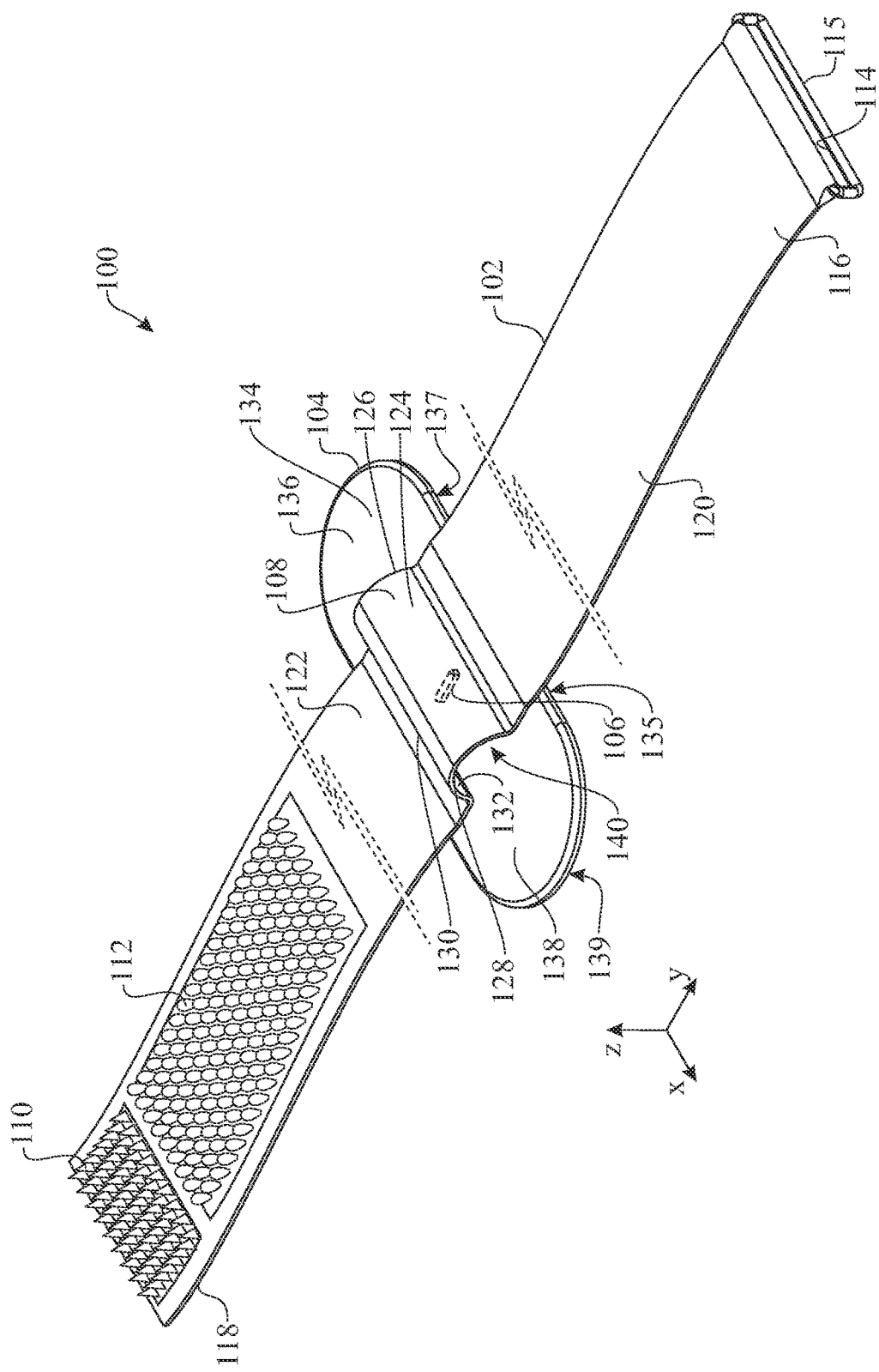
FIG. 1 presents an isometric view of a hose retaining device in accordance with a first illustrative embodiment of the present invention.

With continued reference to FIG. 1, the strap assembly 102 may include a right strap portion 116 and a left strap portion 118 extending in opposite, left and right directions relative to the cavity 140. The right strap portion 116 may include a right upper surface 120, and the left strap portion 118 may include a left upper surface 122. The right strap portion 116 and left strap portion 118 may disconnectably connect to one another to form a loop around body area of a user. For instance, in some embodiments, the right and left strap portions 116 and 118 may disconnectably attach to one another by one or more fasteners providing size-adjustability such that the loop formed by the strap assembly 102 around the user's body portion may be adjusted to different user sizes and/or body areas; for instance and without limitation, the right and left strap portions 116 and 118 may be disconnectably and adjustably connectable to one another by an elongated hook-and-loop fastener. In other embodiments, such as the present embodiment, the right strap portion 116 may include a fastening slot 114 configured to slidingly receive the left strap portion 118 of the strap assembly 102 therethrough, to form a loop around a body portion or area of a user (see, for instance, FIG. 2). As shown, the fastening slot 114 may be provided by a connector 115, which may include a D-ring connector, an elongated O-ring connector, a rectangular connector, etc. The left upper surface 122 may include a hook portion 110 and a loop portion 112, wherein the hook portion 110 and the loop portion 112 are configured to releasably couple. The hook portion 110 may be located distally of the loop portion 112, i.e. closer to a far end of the left strap portion 118 than the loop portion 112. As shown, one or both of the hook portion 110 and the loop portion 112 may be elongated, to allow for size-adjustability of the strap assembly loop obtained by attaching the hook and loop portions 110 and 112 to one another.

The retaining loop 108 may include an outer surface 124 having an upper portion 126, a lower portion 128, and a middle portion 130. The retaining loop 108 may further include an underside 132 facing the cavity 140 formed between the retaining loop 108 and the padding portion 104. As shown for instance in FIG. 4, the cavity 140 may be configured to receive a corrugated tubing 200 having a plurality of valleys or sunken portions 202 and a plurality of peaks, ribbed portions or protruding portions 204. The protruding member 106 may be shaped and sized to at least partially fit inside a sunken portion 202 of the corrugated tubing 200, as will be described in greater detail hereinafter. Further still, the underside 132 of the retaining loop 108 may include an upper portion, a lower portion, and a middle portion, arranged oppositely to the upper portion 126, lower portion 128 and middle portion 130 of the outer surface 124. The underside 132 of the retaining loop 108 may be structured and arranged to form the aforementioned cavity 140 with the top surface 134 of the padding portion 104. For instance, the underside 132 may be formed as continuous or uninterrupted surface, elongately formed along the longitudinal direction x, as shown. In some embodiments, such as the present embodiment, opposite edges of the retaining loop 108 may be fixedly secured to the strap assembly 102.

Figure 2:
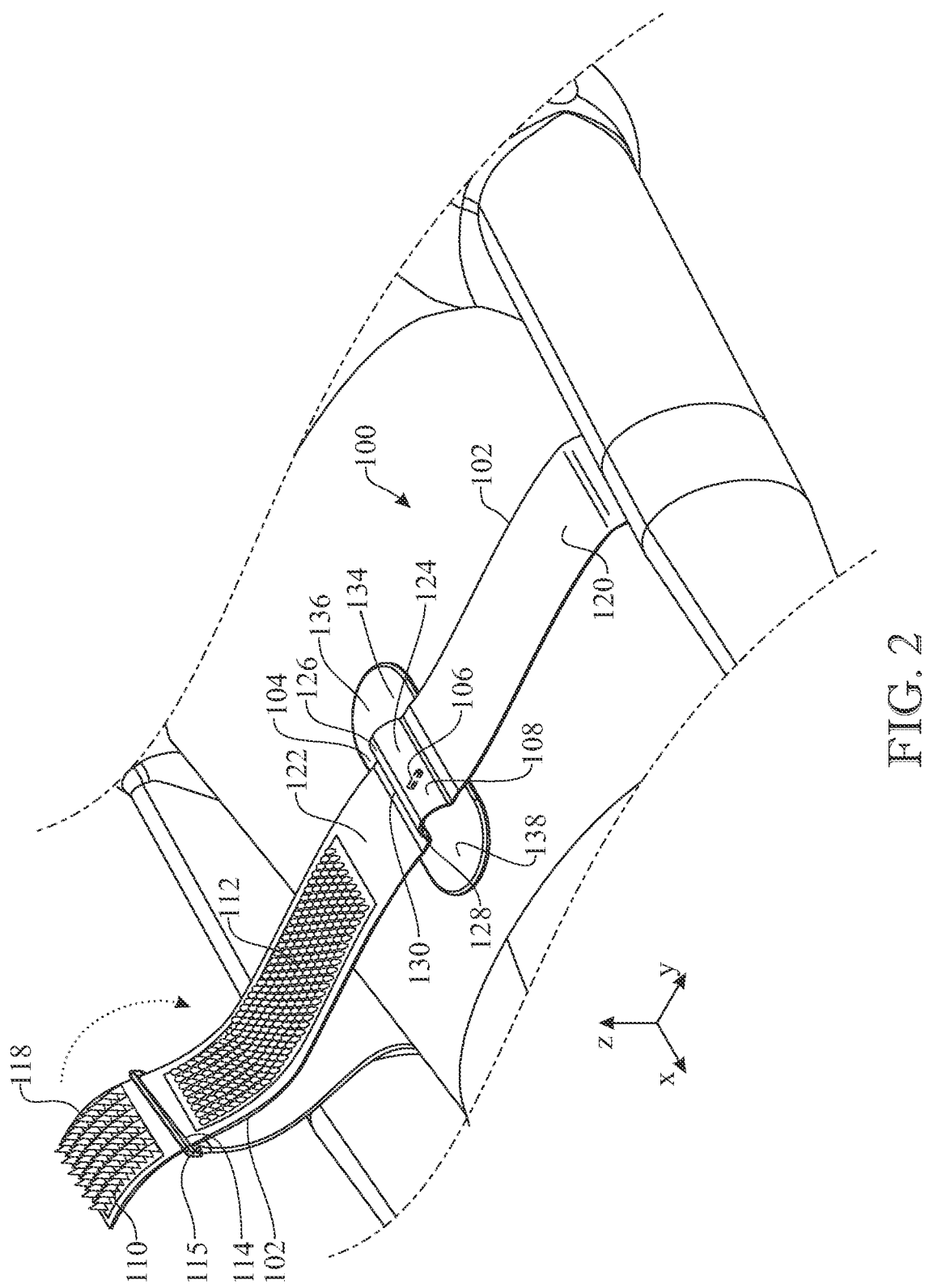
FIG. 2 presents an isometric view of the hose retaining device of FIG. 1, the hose retaining device shown in an exemplary application in which the hose retaining device is placed around a subject's body chest or torso, the hose retaining device shown in an unfastened state.
Figure 3:
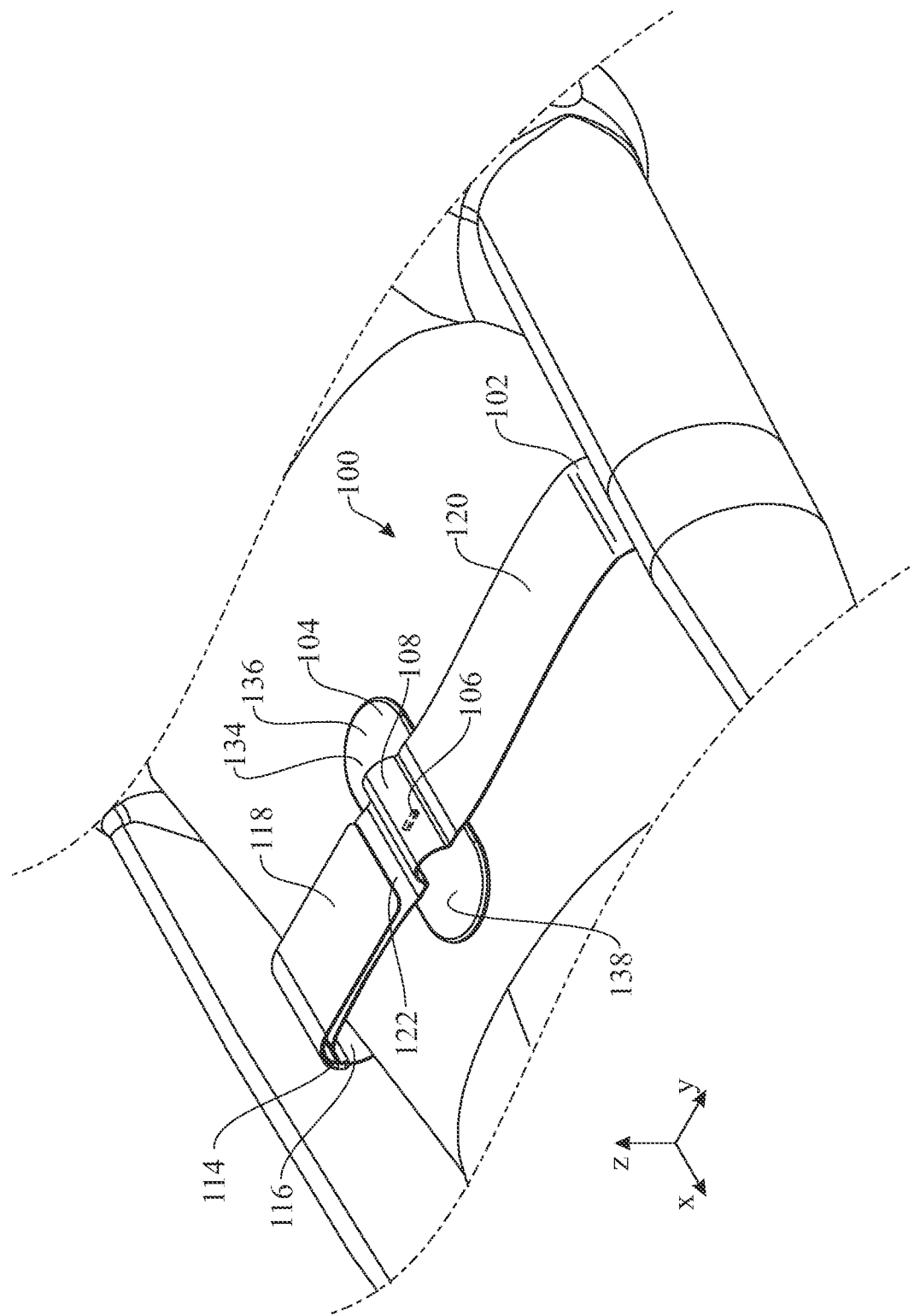
FIG. 3 presents an isometric view of the hose retaining device of FIG. 2, shown in a fastened state.

The illustrations of FIGS. 2-6 show the hose retaining device 100 in operation. With reference initially to FIG. 2, to fasten the hose retaining device 100 around a user, the strap assembly 102 may be extended or wrapped around the user's torso or other body area or body portion. The left strap portion 118 having the hook portion 110 may be inserted or threaded through the fastening slot 114. Next, from the unfastened state of FIG. 2, the left strap portion 118 may be pulled back upon itself to releasably mate the hook portion 110 with the loop portion 112 of the left upper surface 122, to reach a fastened state shown in FIG. 3. The pulling back of the left strap portion 118 upon itself may be selectively carried out to a lesser or greater extent, to adjust the looped strap assembly 102 to different body sizes. The hook-and-look connection between the hook portion 110 and the loop portion 112 is also adjustable by varying the degree of overlap between the hook and loop portions 110 and 112.

Referring next to FIG. 4, once the hose retaining device 100 has been fitted and adjusted to the user's body, a medical tubing or hose may be inserted and extended through the cavity 140 defined between the retaining loop 108 and the padding portion 104, and stabilized by the retaining loop 108. For example, a corrugated hose or tubing 200 of a breathing apparatus or other medical apparatus may be extended through and along the cavity 140 as shown and indicated by arrow A. As shown in FIG. 5, the hose or tubing may be directed, for instance, towards a user's head or neck to facilitate air supply to an air entry port, schematically illustrated at 206.

With continued reference to FIG. 5, once the tubing 200 is connected to the air entry, the tubing 200 remains stabilized at the top central area of the user's torso by the retaining loop 108, through which the tubing 200 extends. The elongated, retaining loop 108 may minimize or prevent lateral swaying of the tubing 200 in left and right directions, i.e. on an x-y plane. In addition, because the retaining loop 108 extends over and along a top side of the tubing 200 (as also shown in FIG. 6), the retaining loop 108 may minimize or prevent vertical swaying of the tubing 200, i.e. swaying in an x-z plane (FIG. 6). Thus, the retaining loop 108 generally maintains the tubing 200 in the desired position defined by the selected orientation of the retaining loop 108 when the hose retaining device 100 is secured to the user's body. As further shown in FIG. 6, the tubing 200 may be snugly received inside the cavity 140, wherein the cavity 140 may have a height (dimension in a vertical direction z, which is perpendicular to the longitudinal direction x and the transverse direction y) which is generally the same or slightly greater than the thickness of the tubing 200, to further stabilize the tubing 200 on the x-z plane; for instance, the retaining loop 108 may be elastically stretchable to slightly compress against the tubing 200, and may be flexible to facilitate inserting the tubing 200 through the cavity 140.

As further shown in FIG. 6, the protruding member 106 may be configured to rest within at least one of the plurality of sunken portions 202 of the corrugated tubing 200. In doing so, the protruding member 106 may prevent a displacement of the tubing 200 relative to the hose retaining device 100 along the longitudinal direction x, allowing the corrugated tubing 200 to remain in a desired position longitudinally about the user. In this way, the hose retaining device 100 may provide significant advantages to a user required to wear a CPAP type mask at night for help with sleep apnea, as the hose retaining device 100 will prevent that the corrugated tubing 200 shifts or pulls against the user as he or she sleeps at night and changes positions in bed. By having the corrugated tubing 200 remain affixed to the user's torso in a desired configuration, the tubing 200 may remain secure and not pull against the breathing mask or present unnecessary discomfort.

The illustrations of FIGS. 7-11 show a hose retaining device 300 in accordance with another illustrative embodiment of the present invention. Similarly to the previous embodiment, the hose retaining device 300 configured to stabilize a medical tube along and/or against a body of a subject.

Figure 7:
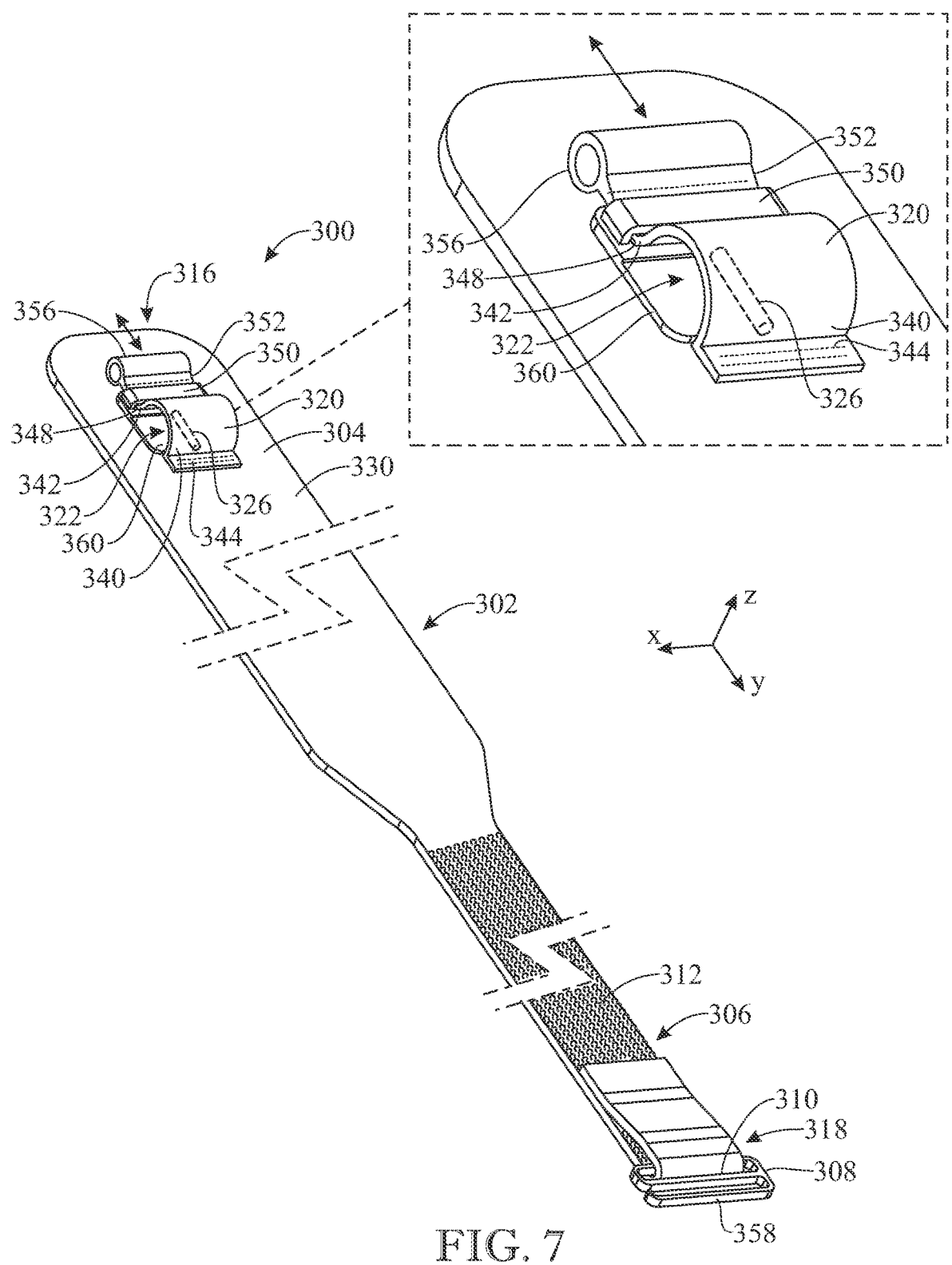
FIG. 7 presents an isometric view of a hose retaining device in accordance with a second embodiment of the present invention.
Figure 11:
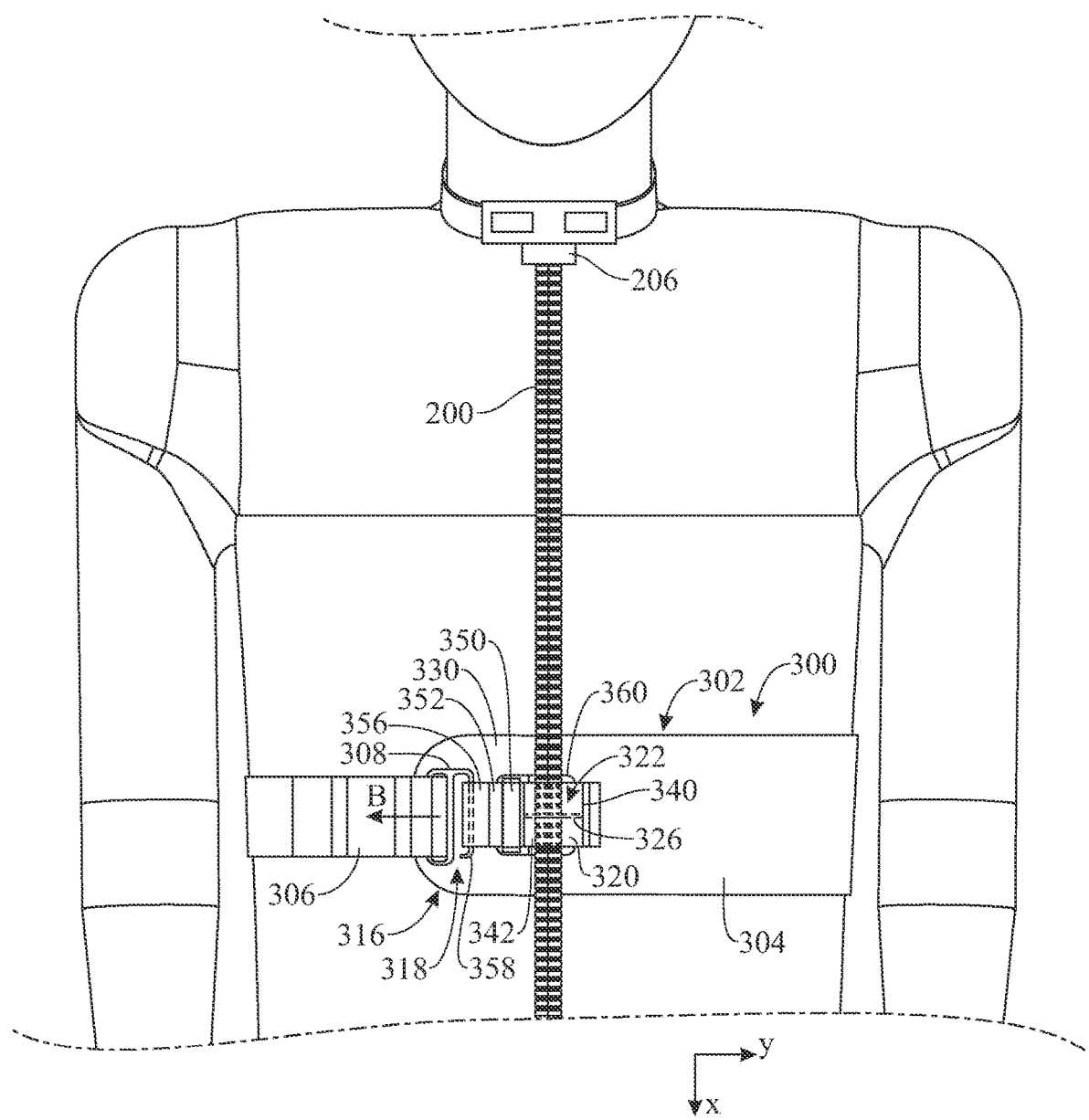
FIG. 11 presents a top plan view of the hose retaining device of FIG. 7, shown fitted around a subject's chest or torso, and retaining a corrugated air supply tube.

With reference initially to FIG. 7, similarly to the previous embodiment, the hose retaining device 300 of the present embodiment includes a strap assembly 302, which is removably positionable and securable around a body area of a user, such as, but not limited to, the chest of a user, as shown for instance in FIG. 11. The hose retaining device 300 further includes a retaining loop 320, which, similarly to the previous embodiment, is carried by the strap assembly 302 such that the strap assembly 302 can position and secure the retaining loop 320 at or near the subject's body part. The retaining loop 320 defines an elongated, through bore or cavity 322. Also similarly to the previous embodiment, the cavity 322 is elongately formed along a longitudinal direction x and is configured to receive a portion of a corrugated tubing 200 therealong.

Figure 8:
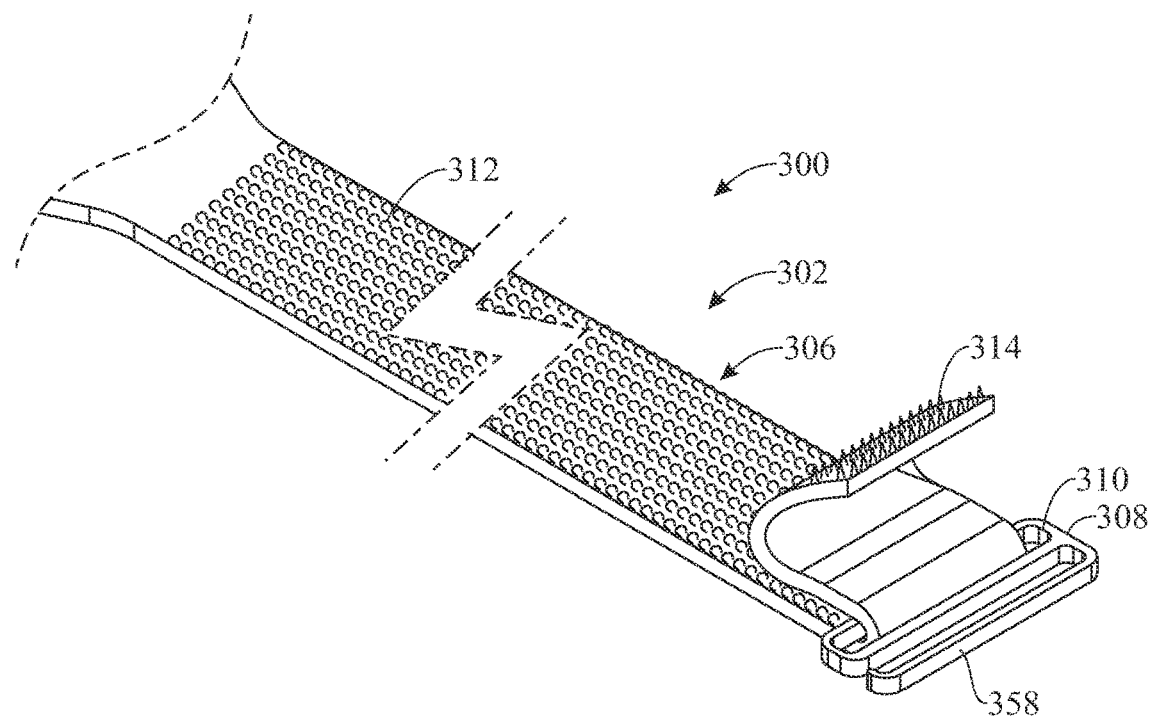
FIG. 8 presents an isometric view of a first end of the strap assembly of the hose retaining device of FIG. 7, demonstrating an adjustable attachment of a looped portion of the first end onto itself.
Figure 9:
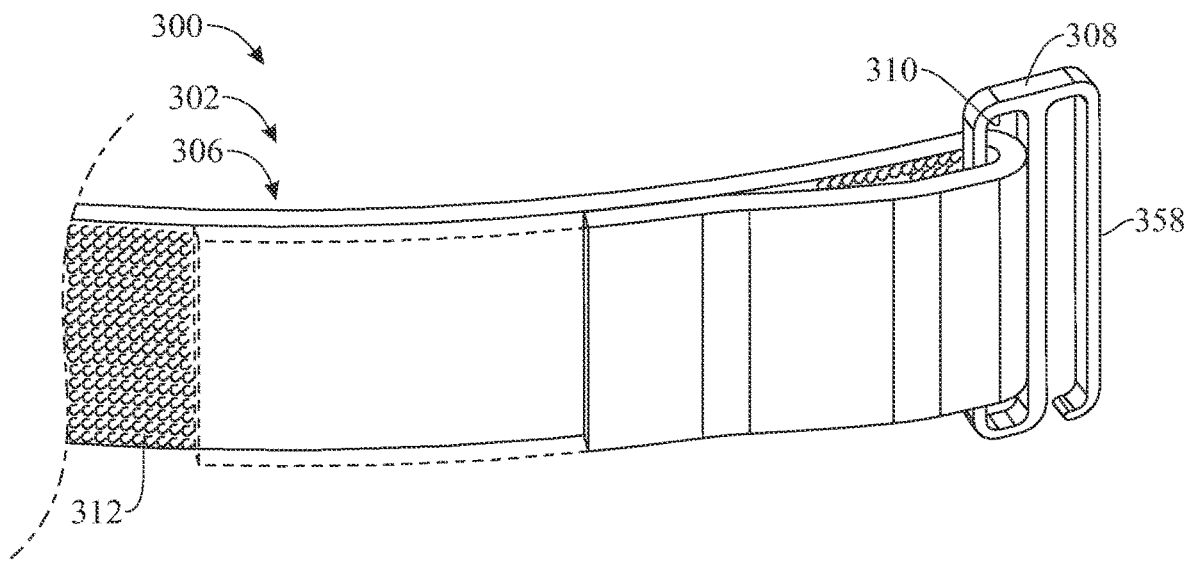
FIG. 9 presents an isometric view of the first end of the strap assembly of FIG. 9, showing the looped portion of the first end folded over and attached onto itself at a specific position to obtain a corresponding size of the strap assembly.

Similarly to the previous embodiment, the strap assembly 302 of the present embodiment is adjustably securable around the body area of the user, such that the user or another person can adjust or select the size of a loop formed by the strap assembly 302 around the body area, to conform to body areas of different sizes, such as when switching the hose retaining device 300 from one person to another, or when attaching the hose retaining device 300 to different body areas of a same user. For example, in the present embodiment, the strap assembly 302 includes a first portion 304 and a second portion 306, which may provide or include opposite free ends 316 and 318, respectively, of the of the strap assembly 302. The second portion 306 of the strap assembly 302 may carry a connector 308. The connector 308 may include a slot 310 for the passing therethrough of the second portion 306 of the strap assembly 302. The second portion 306 may be looped through the slot 310 and attached onto itself, as best shown in FIGS. 8 and 9, to secure the connector 308 to the second portion 306. The second portion 306 may be connected to itself by a hook-and-loop fastener; for example, the second portion 306 may include a loop portion 312 distally followed by a hook portion 314 configured to attach to the loop portion 312 once the second portion 306 has been looped around the connector 308. The hook and loop portions 314 and 312 may be connectable to one another at different overlapping positions in order to adjust the overall length of the strap assembly 302. In some embodiments, the loop portion 312 may be arranged along a section of the strap assembly 302, as shown in FIG. 8. In other embodiments, substantially the entire strap assembly 302 may be made of a loop-fastener type material, such that the hook portion 314 may attach to substantially any area of the strap assembly 302 once the second portion 306 is looped through the slot 310, allowing for increased size adjustability.

Referring again to FIG. 1, similarly to the previous embodiment, the house retaining device 300 of the present embodiment includes a platform 330, to which the retaining loop 320 is affixed. In the present embodiment, the platform 330 is carried by the strap assembly 302 by having the platform 330 integrally formed with the strap assembly 302. As shown, the platform 330 is provided by a generally planar area of the first portion 304 of the strap assembly 302. Similarly to the previous embodiment, the platform 330 is configured to rest against the chest or other body area of the user, to stabilize the retaining loop 320 and maintain the retaining loop 320 adjacent to the body area.

With continued reference to FIG. 1, the retaining loop 320 may further include a first side portion 340 and a second side portion 342, arranged opposite to one another, at opposite sides of the cavity 322. The first side portion 340 may be fixedly secured to the strap assembly 302, such as by a stitching 344, welding, an adhesive, or by having the retaining loop 320 integrally formed with adjacent portions of the strap assembly 302. The first side portion 340 of the retaining loop 320 may be arranged closer to the second portion 306 of the strap assembly 302. In turn, the second side portion 342 of the retaining loop 320 may be slidably received through a guide slot 348 of the strap assembly 302. For instance and without limitation, the guide slot 348 may be defined by a strip-like or bridge-like member 350 protruding outwardly from the generally planar platform 330 of the first portion 304 of the strap assembly 302, such that the guide slot 348 is defined below the bridge-like member 350. As further shown, the cavity 322 may be formed between the first side portion 340 of the retaining loop 320 and the guide slot 348. The second side portion 342 of the retaining loop 320 may include a free end 352 extending outward of the guide slot 348, oppositely to the cavity 322. The free end 352 of the retaining loop 320 may be connectable to the second portion 306 of the strap assembly 302. For instance and without limitation, the free end 352 of the retaining loop 320 may include a second loop 356, and the second portion 306 of the strap assembly 302 may be disconnectably attached to the second loop 356. In some embodiments, such as the present embodiment, the disconnectable connection between the second portion 306 of the strap assembly 302 and the second loop 356 may be provided between a hook 358 comprised in the connector 308, the hook 358 configured to hook onto the second loop 356.

Figure 12:
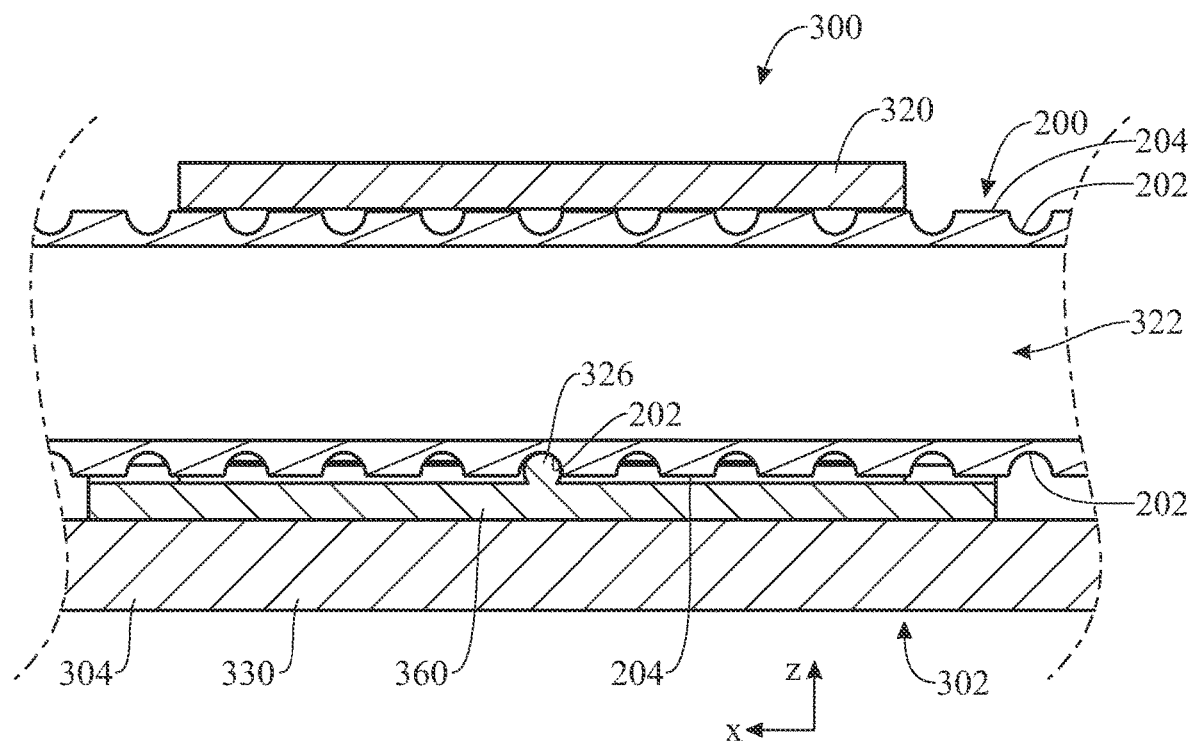
FIG. 12 presents a cross-sectional side elevation view of the retaining loop, padding portion, and protruding member

Turning to FIGS. 7 and 12, similarly to the previous embodiment, the hose retaining device 300 of the present embodiment further includes a protruding member 326 configured to frictionally engage a valley or sunken portion 202 of the corrugated tubing 200 to block a displacement of the corrugated tubing 200 in the longitudinal direction x along the cavity 322 and relative to the strap assembly 302. Also similarly to the previous embodiment, the protruding member 326 may protrude into the cavity 322, allowing the engagement between the protruding member 326 and the corrugated tubing 200 to be concealed and protected by the retaining loop 320, contributing to prevent unwanted or inadvertent separation of the corrugated tubing 200 from the protruding member 326. In preferred embodiments, such as the present and previous embodiments, the protruding member 326 is in fact arranged within the cavity 322. For instance, the protruding member 326 may be affixed to the strap assembly, and more specifically, to the platform 330, and arranged facing the cavity 322 and facing the retaining loop 320; in a non-limiting example, the protruding member 326 may be affixed to a support plate 360 which is adhered or otherwise secured to the platform 330 of the first portion 304 of the strap assembly 302. In some embodiments, such as the present embodiment, the bridge-like member 350 may be integrally-formed with the support plate 360, and jointly manufactured, for instance, of a relatively rigid material than a remainder of the strap assembly 302 including the first and second portions 304 and 306, to obtain a generally non-deformable guide slot 348.

Figure 10:
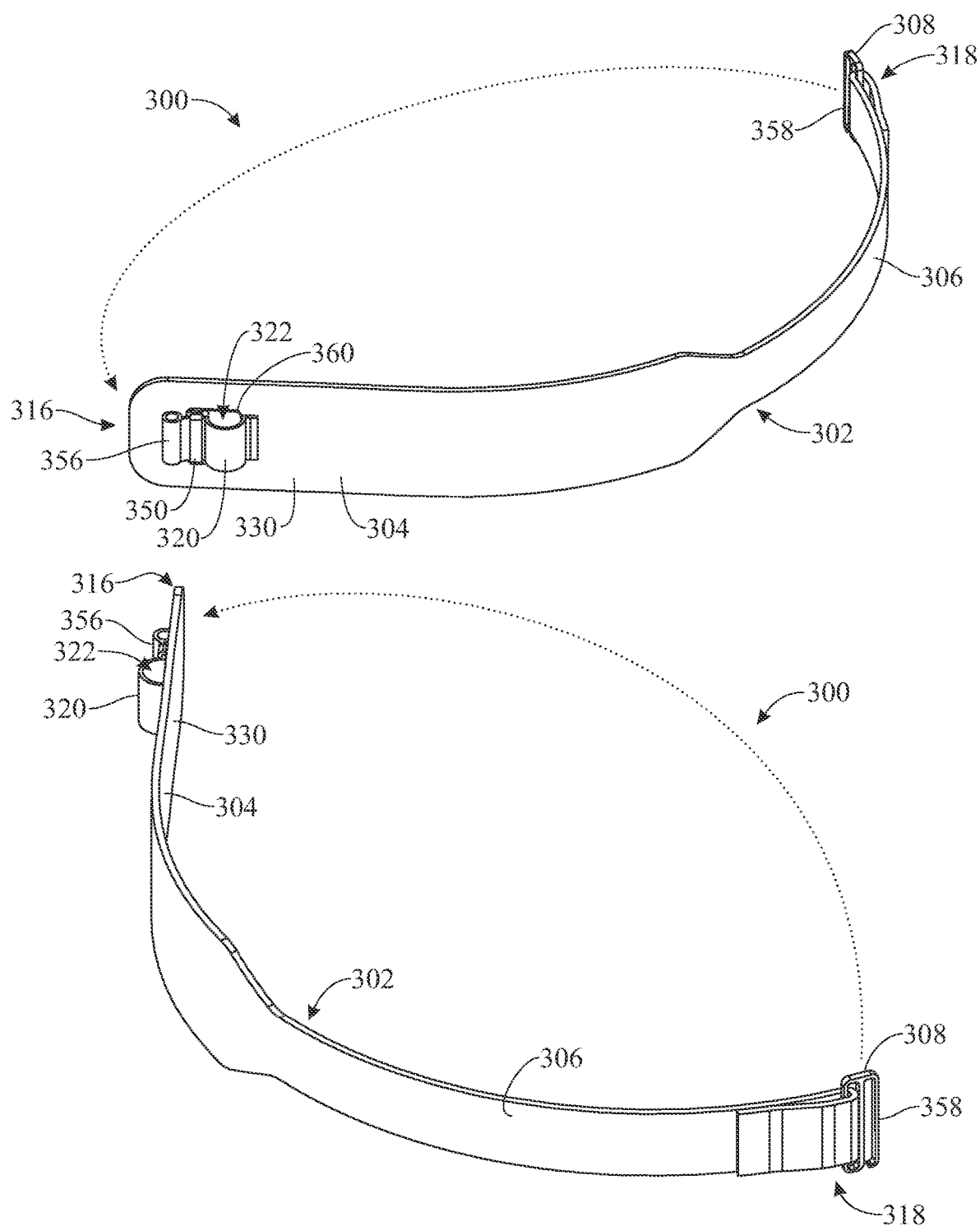
FIG. 10 presents two perspective views of the strap assembly of FIG. 7, illustrating how the first end of the strap assembly is disconnectably secured to an opposite, second end of the strap assembly.

Operation of the hose retaining device 300 will now be described with reference to FIGS. 8-12. Turning initially to FIGS. 10 and 11, the strap assembly 302 is wrapped around a user's chest or other body area and the free ends 316 and 318 of the strap assembly 302 are pulled towards one another, as best shown in FIG. 10. Next, the second portion 306 of the strap assembly 302 is connected to the first portion 304 of the strap assembly 302 at the free ends 316 and 318 by engaging the hook 358 of the connector 308 at the free end 318 with the second loop 356 arranged at or proximate the free end 316. The user or operator may then insert the corrugated tubing 200 through the cavity 322, as was heretofore described with reference to the previous embodiment. Once the corrugated tubing 200 is positioned in place and connected to the appropriate terminals (e.g., entry port 206), the user may tighten the strap assembly 302 by adjusting the overlapping-onto-itself of the second portion 306 of the strap assembly 302 as shown in FIGS. 8 and 9, to achieve the desired tightness and corresponding strap assembly length. As the user or operator tightens the strap assembly 302, the hook 358 pulls on the second loop 356, and thus pulls the second loop 356 of the retaining loop 320 away from the fixed, first side portion 340 of the retaining loop 320, as indicated by arrow B in FIG. 11. Pulling of the second loop 356 causes the first side portion 340 of the retaining loop 320 to slide outward (in the direction of arrow B) through the guide slot 348, reducing the size of the cavity 322 provided by the retaining loop 320 and causing the retaining loop 320 to compress against the corrugated tubing 200. By pressing against the corrugated tubing 200, the retaining loop 320 at least partially prevents swaying of the corrugated tubing 200 relative to the strap assembly 302 and relative to the longitudinal direction x. In addition, as shown in FIG. 12, the protruding member 326 frictionally engages a valley or sunken portion 202 of the corrugated tubing 200 and thereby blocks a displacement of the portion of the corrugated tubing 200 in the longitudinal direction x along the cavity 322 and relative to the strap assembly 302. Furthermore, similarly to the previous embodiment, compression of the retaining loop 320 against the corrugated tubing 200 promotes the engagement between the protruding member 326 and the sunken portion 202, and increases longitudinal locking of the corrugated tubing 200. These aforementioned effects are rapidly and easily achieved by simply tightening the strap assembly 302 as described heretofore.

The hose retaining device of the present disclosure thus provides an effective solution for keeping a tubing or hose, and most particularly a corrugated tubing, commonly used in conjunction with a breathing assistance device, in a correct position to increase comfort and stability. As disclosed, it is common for users who require breathing assistance due to low oxygen intake, a tracheostomy, or sleep apnea just to name just a few conditions to experience discomfort or even breathing problems as a result of their breathing tube being compromised. This can be especially dangerous and troublesome at night for people who may wear a CPAP mask as it is essential that the mask form a tight seal about the face of the user. When breathing tubes get pulled or leveraged against the user, the mask can easily be pulled away from the user's face, thereby creating an inefficient, uncomfortable, and potentially dangerous situation for the user. The disclosed hose retaining device helps to eliminate these types of situations, allowing the user to breathe comfortably and without disruptions.

In some embodiments, the hose retaining device may be disposable. In other embodiments, the hose retaining device may be reusable and preferably washable. For instance and without limitation, the hose retaining device 100 may be disposable and the hose retaining device 300 may be reusable and preferably washable.

Further embodiments are contemplated in which different fasteners may be used in the place of the hook portion and the loop portion. Other fastening means are hereby contemplated, including but not limited to, Q-clip and loop, snaps, buckles, clamps, zippers, etc. In addition, the padding portion may also be configured in different shapes and sizes to accommodate varying needs of the user.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A hose retaining device, comprising:
   a strap assembly, comprising a first portion and a second portion, the first portion comprising a first end of the strap assembly and the second portion comprising a second end of the strap assembly opposite to the first end of the strap assembly;
   a retaining loop, carried by the first portion of the strap assembly, the retaining loop defining a cavity, the cavity elongately formed along a longitudinal direction and configured to receive a portion of a corrugated tubing therealong; and
   a protruding member shaped and sized to fit into a valley of the portion of the corrugated tubing to thereby cause a blocking of a displacement of the portion of the corrugated tubing in the longitudinal direction along the cavity and relative to the strap assembly; wherein
   the strap assembly is removably positionable in a mounted configuration in which the strap assembly extends around a body area of a user and is secured in place by the second end of the strap assembly being connected to the retaining loop; wherein
   in the mounted configuration of the strap assembly, the retaining loop at least partially prevents swaying of the corrugated tubing relative to the strap assembly and relative to the longitudinal direction, and the second end of the strap assembly pulls on the retaining loop to press the retaining loop against said portion of the corrugated tubing to thereby maintain said protruding member engaged with said valley of said portion of the corrugated tubing towards one another thereby maintaining said blocking of said displacement of the portion of the corrugated tubing; and
   wherein the retaining loop comprises opposite first and second side portions, wherein the first side portion of the retaining loop is fixedly secured to the first portion of the strap assembly, and the second side portion of the retaining loop extends from the first side portion of the retaining loop and is slidably received through and outward of a guide slot of the strap assembly, the cavity formed between the first side portion of the retaining loop and the guide slot, the second side portion ending in a free end opposite to the first side portion of the retaining loop and connectable to the second end of the strap assembly, wherein, in the mounted configuration of the strap assembly, the second end of the strap assembly is connected to the free end of the second side portion of the retaining loop and is configured to pull on said free end to slide the retaining loop further outward of the guide slot, and thereby reduce a size of the cavity, responsibly to tightening of the strap assembly around the body area.

2. The hose retaining device of claim 1, wherein the body area is a chest area.

3. The hose retaining device of claim 1, wherein the strap assembly is adjustably securable around the body area of the user.

4. The hose retaining device of claim 1, further comprising a platform carried by the strap assembly, the platform configured to rest against the body area of the user, wherein the retaining loop is affixed to the platform.

5. The hose retaining device of claim 1, wherein the free end of the second side portion of the retaining loop comprises a second loop, to which the second portion of the strap assembly is disconnectably attachable.

6. The hose retaining device of claim 5, wherein the second portion of the strap assembly comprises a hook, configured to disconnectably hook onto the second loop of the retaining loop.

7. The hose retaining device of claim 5, wherein the second portion of the strap assembly is disconnectably looped onto itself to adjust a length of the strap assembly.

8. The hose retaining device of claim 7, wherein the second portion of the strap assembly comprises a hook, configured to disconnectably hook onto the second loop of the retaining loop, and further wherein the second portion of the strap assembly is slidably looped through a slot of said hook and disconnectably attached to itself.

9. The hose retaining device of claim 1, wherein the protruding member protrudes into the cavity.

10. The hose retaining device of claim 9, wherein the protruding member is arranged within the cavity.

11. The hose retaining device of claim 10, wherein the protruding member is affixed to the strap assembly and arranged facing the cavity and facing the retaining loop.

12. The hose retaining device of claim 1, further comprising a connector configured to disconnectably connect the second end of the strap assembly to the retaining loop, and further wherein, in the mounted configuration of the strap assembly:
   the second end of the strap assembly is disconnectably secured to the retaining loop by the connector, and
   the connector is arranged over the first portion of the strap assembly such that the first portion separates the connector from the body area of the user.

13. The hose retaining device of claim 12, wherein the connector comprises a hook.

14. A hose retaining device, comprising:
- a strap assembly, adjustably securable around a body area of a user, the strap assembly comprising a first portion and a second portion, the first portion comprising a first end of the strap assembly and the second portion comprising a second end of the strap assembly opposite to the first end of the strap assembly;
- a retaining loop, carried by the first portion of the strap assembly, the retaining loop defining a cavity, the cavity elongately formed along a longitudinal direction and configured to receive a portion of a corrugated tubing therealong;
- a protruding member shaped and sized to fit into a valley of the portion of the corrugated tubing to thereby cause a blocking of a displacement of the portion of the corrugated tubing in the longitudinal direction along the cavity and relative to the strap assembly; and
- a connector configured to disconnectably connect the second end of the strap assembly to the retaining loop; wherein the strap assembly is removably positionable in a mounted configuration in which the strap assembly extends around the body area of the user and is secured in place by the second end of the strap assembly being connected to the retaining loop by the connector; wherein in the mounted configuration of the strap assembly:
the connector is arranged over the first portion of the strap assembly such that the first portion separates the connector from the body area of the user, the retaining loop at least partially prevents swaying of the corrugated tubing relative to the strap assembly and relative to the longitudinal direction, and the second end of the strap assembly pulls on the retaining loop to press the retaining loop against said portion of the corrugated tubing to thereby maintain said protruding member engaged with said valley of said portion of the corrugated tubing towards one another thereby maintaining said blocking of said displacement of the portion of the corrugated tubing; and wherein the retaining loop comprises opposite first and second side portions, wherein the first side portion of the retaining loop is fixedly secured to the first portion of the strap assembly, and the second side portion of the retaining loop extends from the first side portion of the retaining loop and is slidably received through and outward of a guide slot of the strap assembly, the cavity formed between the first side portion of the retaining loop and the guide slot, the second side portion ending in a free end opposite to the first side portion of the retaining loop and connectable to the second end of the strap assembly, wherein, in the mounted configuration of the strap assembly, the second end of the strap assembly is connected to the free end of the second side portion of the retaining loop and is configured to pull on said free end to slide the retaining loop further outward of the guide slot, and thereby reduce a size of the cavity, responsibly to tightening of the strap assembly around the body area.

* * * * *